United States Patent
Herrmann et al.

[11] Patent Number: 5,961,533
[45] Date of Patent: Oct. 5, 1999

[54] SURGICAL INSTRUMENT

[75] Inventors: Gebhard Herrmann, Irndorf; Frank Püschel, Tuttlingen, both of Germany

[73] Assignee: Aesculap AG & Co. KG, Tuttlingen, Germany

[21] Appl. No.: 08/989,440

[22] Filed: Dec. 12, 1997

[30] Foreign Application Priority Data

Dec. 14, 1996 [DE] Germany ............... 196 52 163

[51] Int. Cl.$^6$ .................................................. A61B 17/00
[52] U.S. Cl. ............................................................. 606/174
[58] Field of Search .................................. 606/174–175, 606/139, 142, 143, 167, 172, 181, 182; 227/901, 902

[56] References Cited

U.S. PATENT DOCUMENTS

| | | |
|---|---|---|
| 2,708,437 | 5/1955 | Hutchins . |
| 2,894,324 | 7/1959 | Hardin . |
| 4,602,631 | 7/1986 | Funatsu ................................. 606/142 |
| 5,002,554 | 3/1991 | Korber ................................. 606/174 |
| 5,104,397 | 4/1992 | Vasconcelos et al. . |
| 5,122,150 | 6/1992 | Puig ................................. 606/142 |
| 5,269,790 | 12/1993 | Funatsu ................................. 606/142 |
| 5,282,817 | 2/1994 | Hoogeboom et al. ................... 606/205 |

FOREIGN PATENT DOCUMENTS

| | | |
|---|---|---|
| 31 46 426 | 7/1982 | Germany . |
| 31 03 352 | 10/1982 | Germany . |
| 34 19 928 | 3/1987 | Germany . |
| WO 84/01281 | 4/1984 | WIPO . |

*Primary Examiner*—Michael Buiz
*Assistant Examiner*—Vikki Trinh
*Attorney, Agent, or Firm*—Barry R. Lipsitz; Ralph F. Hoppin

[57] ABSTRACT

In order to make it possible, in a surgical instrument comprising a tubular shaft with two tools pivotable towards one another at its distal end, these tools being pivotable relative to one another by means of a grip section at the proximal end of the tubular shaft via a transfer member arranged in the tubular shaft, to use the tools in a region arranged laterally of the instrument even with a simple construction it is suggested that the pivot axis of the tools extend concentrically to the longitudinal axis of the tubular shaft, that one tool be securely connected to the tubular shaft and the other securely connected to the transfer member, that the transfer member be a core mounted in the tubular shaft for rotation about its longitudinal axis, and that the grip section comprise two grip elements pivotable towards one another, one of these elements being connected to the tubular shaft and the other to the transfer member.

19 Claims, 5 Drawing Sheets

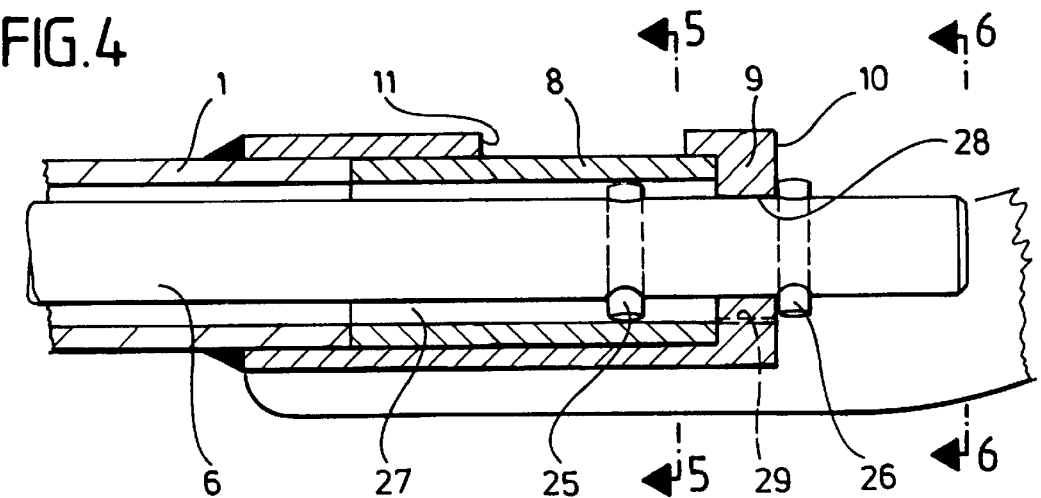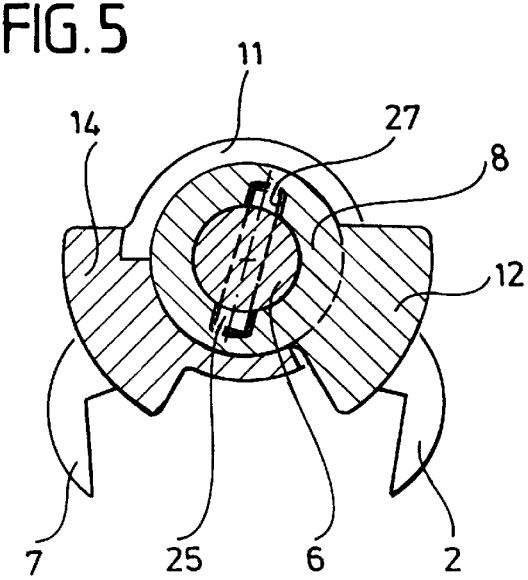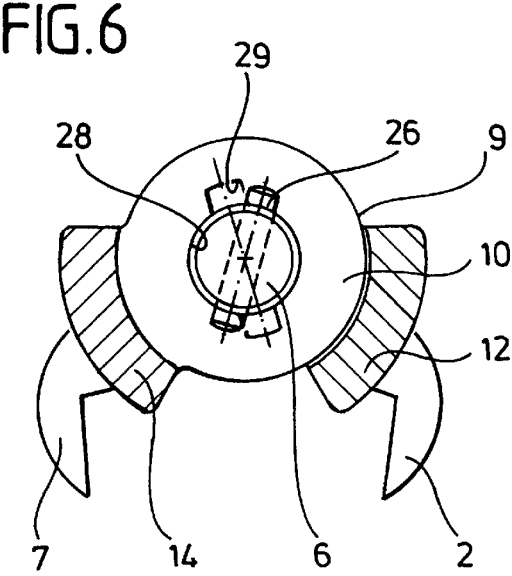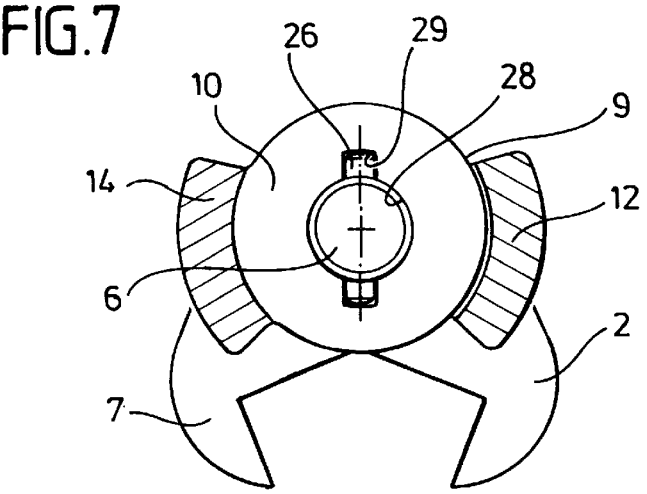

SURGICAL INSTRUMENT

BACKGROUND OF INVENTION

The invention relates to a surgical instrument comprising a tubular shaft with two tools pivotable towards one another at its distal end, these tools being pivotable relative to one another by means of a grip section at the proximal end of the tubular shaft via a transfer member arranged in the tubular shaft.

Surgical instruments of this type are used in many different ways, for example as scissors, grasping forceps, suture-needle holders, punches or clip applicators. In this respect, it is customary for the two tools to be pivotable about an axis extending transversely to the longitudinal axis of the tubular shaft. As a result, the applicability of these instruments can, in certain circumstances, be restricted, particularly when they are used in endoscopic operations.

It is known to design instruments of this type so as to be angled at the distal end but for this purpose complicated devices are required which make such a bending of the tubular shaft and the tools mounted thereon possible.

SUMMARY OF THE INVENTION

The object of the invention is to develop a surgical instrument of the generic type such that the tools pivotable towards one another can be designed to project laterally in a simple manner.

This object is accomplished in accordance with the invention, in a surgical instrument of the type described at the outset, in that the pivot axis of the tools extends concentrically to the longitudinal axis of the tubular shaft, that one tool is securely connected to the tubular shaft and the other is securely connected to the transfer member, that the transfer member is a core mounted in the tubular shaft for rotation about its longitudinal axis and that the grip section comprises two grip elements pivotable towards one another, one of these grip elements being connected to the tubular shaft and the other to the transfer member.

A particularly simple construction results in this manner since it is sufficient to provide a tubular shaft and a core mounted for rotation therein, wherein the tubular shaft bears one tool and the core the other tool. When the core is rotated in relation to the tubular shaft, the two tools are also rotated in relation to one another, namely about the longitudinal axis of the tubular shaft. The rotation of tubular shaft and core can be accomplished simply by way of the two grip elements, one of which is connected to the core and one to the tubular shaft. With such an instrument it is possible to use the tools laterally next to the tubular shaft, in contrast to those instruments, with which the tools extend in longitudinal direction of the tubular shaft and can be used only in front of the tubular shaft.

It is advantageous when the grip elements are forced apart by a spring so that the operator must cause the tools to close contrary to the force of the spring.

In the preferred embodiment, this spring can comprise two clip springs which abut on one another, each form an extension of a grip element and are arranged to be laterally offset in relation to the axis of rotation of the grip elements. These clip springs can, moreover, be releasably connected to one another at their free ends, for example by a lug-shaped extension of the one clip spring engaging in an opening of the other clip spring.

It is, in addition, advantageous when the grip elements can be fixed relative to one another in an intermediate position of their path of movement by means of a rotation blocking means. Rotation blocking means are known in the case of surgical instruments; in this respect, these are interlocking means which first of all prevent any distancing between the two grip elements when the two grip elements come closer to one another but are released when the two grip elements move even closer so that the grip elements can then return to the initial position at a distance from one another. These rotation blocking means can work in one intermediate position or with several intermediate positions; in this case, the person skilled in the art has available different constructions of rotation blocking means which are known per se.

In a preferred embodiment, it is provided for a sleeve to be mounted in the tubular shaft at its proximal end so as to be rotatable and axially non-displaceable, for the tubular shaft to have in the outer wall in the region of the sleeve a window, through which the sleeve is connected with one of the two grip elements, and for the sleeve to be non-rotatably connected to the core.

This sleeve thus forms a bearing sleeve, on the one hand, for the core and, on the other hand, for the grip element connected to the core. The sleeve itself can continue as far as the distal end of the tubular shaft; in this case, the sleeve itself forms the core. In a particularly preferred embodiment, it is, however, provided for the sleeve and the core to be connected with one another as a result of form-locking so as to be non-rotatable but axially displaceable. This solution has the advantage that the core can be separated from the sleeve in axial direction, i.e. the core can be withdrawn out of the tubular shaft in distal direction so that the instrument can be disassembled for cleaning purposes.

The form-locking connection can be formed, for example, by a tongue-and-groove connection, wherein the tongue is preferably formed by at least one radially projecting pin. In the inserted state, the core is thus caused to rotate when the sleeve is rotated in relation to the tubular shaft by the pivoting of the grip element securely connected to it.

It is also possible for the form-locking connection to be formed by at least one flattened area of the circular cross section of the core and a complementary internal cross-sectional shape of the sleeve.

In order to define exactly the relative position of the two tools in relation to one another, it is provided, in addition, for the core to bear a stop which limits the insertion depth of the core into the tubular shaft in proximal direction.

Furthermore, it is advantageously provided for the core to bear a stop which interacts with the tubular shaft and secures the core inserted completely into the tubular shaft against any displacement in distal direction. As a result of the two stops described, the core is fixed in position in relation to the tubular shaft in axial direction.

In this respect, it is advantageous when the stop securing the core against any displacement in distal direction is releasable so that the disassembly of the instrument described above can take place once this stop is released by withdrawing the core in distal direction.

Even in the case of a non-releasable stop, such a withdrawal is possible when, according to a preferred embodiment, it is provided for the stop to be able to slide past the tubular shaft in an intermediate position of the rotary movement of the core in relation to the tubular shaft and thus make a displacement of the core in relation to the tubular shaft in distal direction possible only in this intermediate position. Core and tubular shaft are, in this construction, connected to one another like a bayonet; this bayonet-like connection may be released only in a quite specific intermediate position of the core.

The stop can, in a preferred embodiment, be a projection which protrudes radially from the core and, in an intermediate position, is aligned with a radial extension of a central opening at the proximal end wall of the tubular shaft; in particular, the projection can thereby be a radially projecting pin.

In a different embodiment, it is provided for the core and the opening to have a non-circular, complementary cross section which is congruent in the intermediate position. In this case, as well, the axial displacement of the core in distal direction is possible only in the intermediate position.

While the instrument as described can bear tools of the most varied kinds, which interact with one another, for example, scissors elements, branches of forceps etc., it is particularly advantageous for the two tools to be designed as arms of a clip applicator, for example a clip applicator for aneurysm clips.

The following description of preferred embodiments of the invention serves to describe the invention in greater detail in conjunction with the drawings.

BRIEF DESCRIPTION OF THE DRAWINGS

FIG. 4: an enlarged view of section A in FIG. 3;

FIG. 5: a sectional view along line 5—5 in FIG. 4;

FIG. 6: a sectional view along line 6—6 in FIG. 4 with a core locked in axial direction;

FIG. 7: a view similar to FIG. 6 with a core displaceable in axial direction;

DETAILED DESCRIPTION OF THE INVENTION

Figure 1:
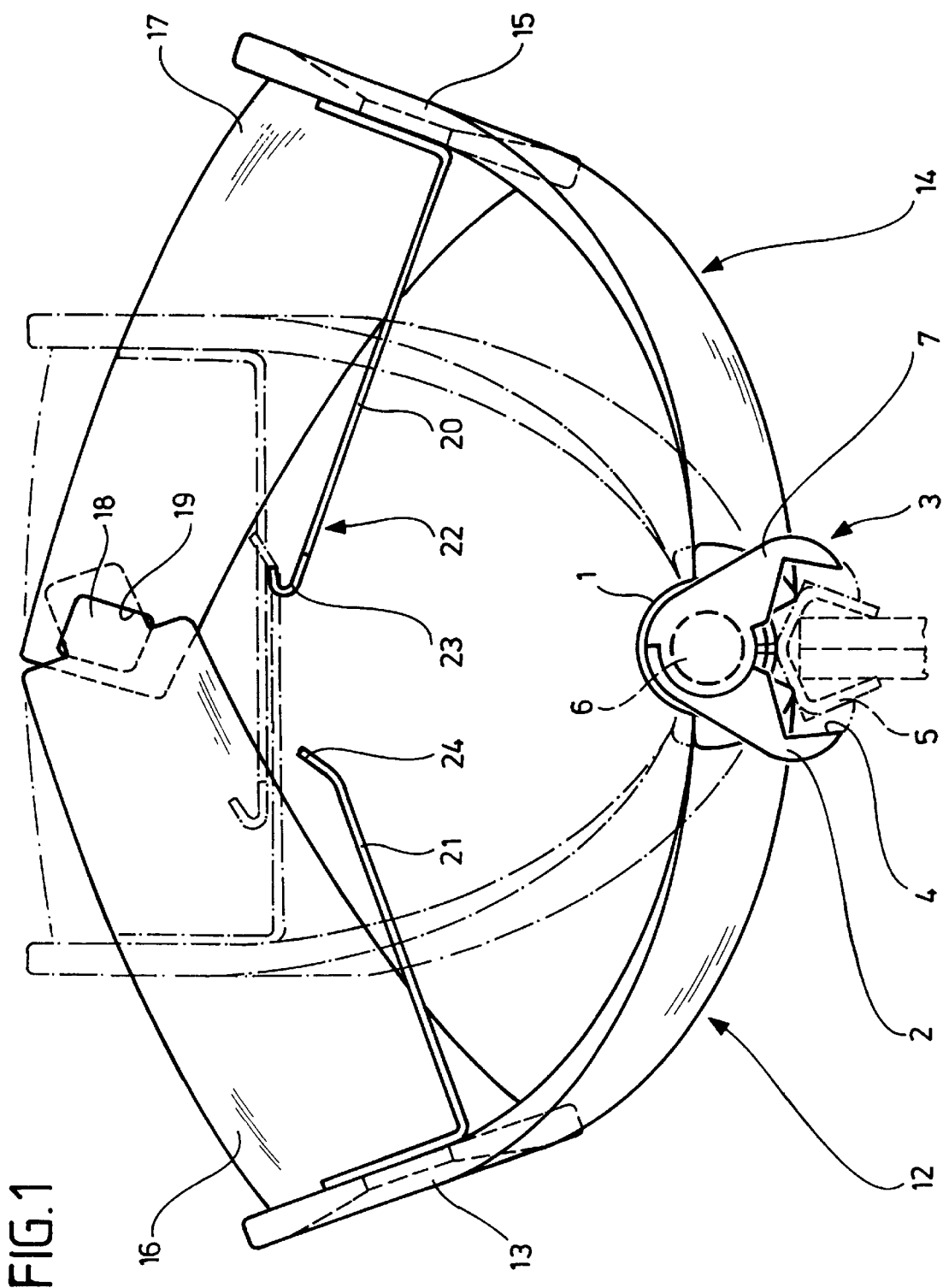
FIG. 1: a front view of a surgical instrument used as a clip applicator with tools rotatable about the longitudinal axis of the tubular shaft.
Figure 2:
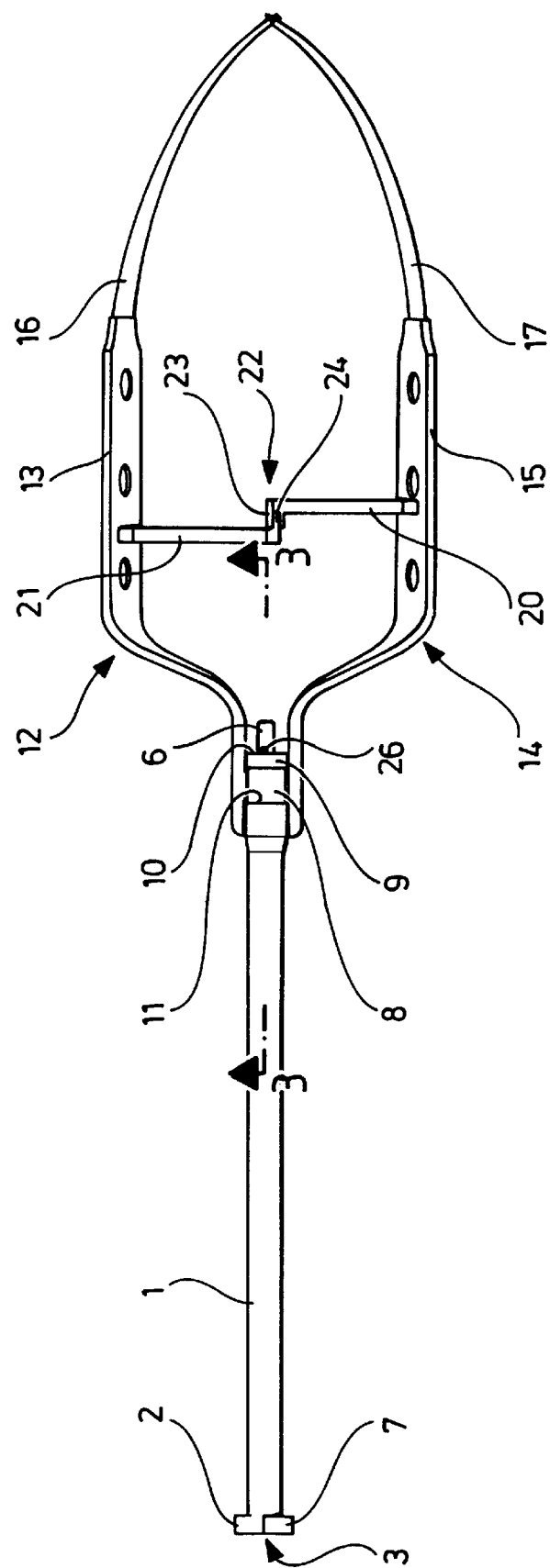
FIG. 2: a plan view of the instrument of FIG. 1.
Figure 3:
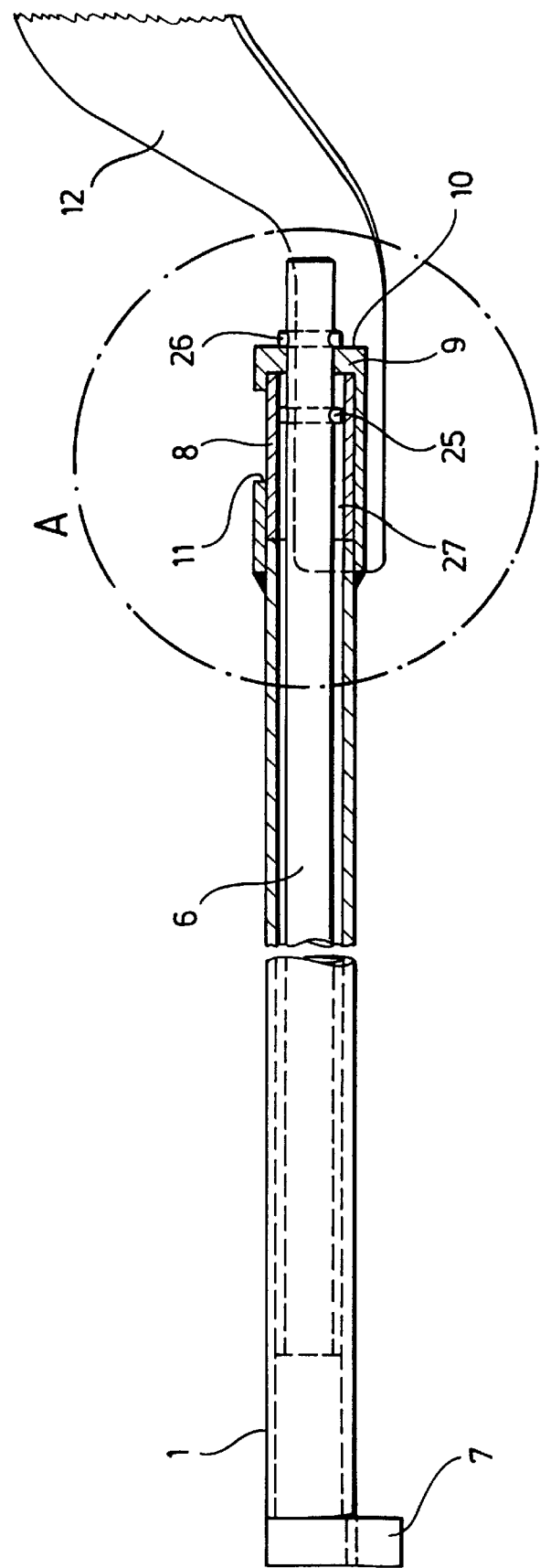
FIG. 3: an enlarged sectional view along line 3—3 in FIG. 2.

The surgical instrument illustrated in FIGS. 1 to 7 comprises an elongated tubular shaft 1 which is securely connected at its distal end with a laterally projecting arm 2 of a clip applicator tool 3. This arm 2 has at its inner side a recess 4 which is rectangular in cross section and forms a contact surface for a surgical clip 5.

A rod-shaped core 6 is mounted in the interior of the tubular shaft 1 for rotation about the longitudinal axis of the tubular shaft. This core bears at its distal end protruding out of the tubular shaft 1 a second arm 7 which is designed in mirror image to the arm 2 and forms together with it the clip applicator tool 3. Both arms 2 and 7 are arranged in a plane at right angles to the longitudinal axis of the tubular shaft and thus protrude laterally beyond the outer contour of the tubular shaft 1.

At its proximal end, a sleeve 8, which is inserted into the tubular shaft 1 and has a cylindrical hood 9 engaging over it, is mounted in the tubular shaft 1 so as to be rotatable. This cylindrical hood 9 forms part of the tubular shaft 1 and is permanently connected to the tubular portion of the tubular shaft 1, for example, by welding after insertion of the sleeve 8. The hood 9 engages over the sleeve 8 by means of an end wall 10 and thereby secures the sleeve 8 in the interior of the tubular shaft 1 in axial direction. The hood 9 has a lateral window 11 which extends over a larger circumferential area and through which a grip element 12 enters the interior of the tubular shaft 1 and is there securely connected to the sleeve 8 in a permanent manner. The grip element 12 extends, proceeding from the point of connection with the sleeve 8, first of all parallel to the longitudinal direction of the tubular shaft 1 in proximal direction and then merges into a gripping area 13 which extends parallel to the longitudinal direction of the tubular shaft 1 and is offset laterally and downwards in relation to the longitudinal axis of the tubular shaft 1.

A second, symmetrically constructed grip element 14 is securely connected to the tubular shaft 1 opposite the first grip element 12, namely such that the gripping areas 13 and 15, respectively, of the two grip elements 12 and 14 extend parallel to one another. When the gripping areas 13 and 15 are pressed towards one another, this leads to a rotation of the sleeve 8 in the interior of the tubular shaft 1.

A coil spring 16 and 17, respectively, bent in the shape of an arc adjoins each of the gripping areas 13 and 15 of the two grip elements 12 and 14, respectively; these two coil springs 16 and 17 are releasably connected to one another at their free ends in that a lug-shaped projection 18 on one coil spring engages in a recess 19 of the other coil spring (FIG. 1). The two coil springs 16 and 17 are thus supported on one another and move the two gripping areas 13 and 15 away from one another so that the sleeve 8 and the tubular shaft 1 are thereby moved into a first relative angular position which is to be designated as rest position. The gripping areas 13 and 15 can be brought closer to one another contrary to the action of the two coil springs 16 and 17, and the sleeve 8 and the tubular shaft 1 are thereby also rotated relative to one another; when the gripping areas 13 and 15 have approached one another completely, the sleeve 8 and the tubular shaft 1 are in a so-called operative position.

The two grip elements 12 and 14 can be fixed in an intermediate position arranged between the rest position and the operative position; for this purpose, the two grip elements 12 and 14 each bear at their inner surfaces facing one another a resilient arm 20 and 21, respectively, which together form a rotation blocking means 22. The two arms 20 and 21 are, altogether, of an L-shaped design; one of these L-shaped projections 23 is bent in the shape of a hook so that the other projection 24 can engage behind this hook-shaped projection 23 and thereby prevent the two gripping areas 13 and 15 from moving apart from one another. When the two gripping areas are brought even closer together, the projections 23 and 24 move apart from one another again. During the subsequent opening of the grip elements 12 and 14, the projection 24 then slides away over the projection 23 so that a renewed engagement on this hook-shaped projection 23 is avoided. A hooking together therefore results only when the two gripping areas are brought slowly closer to one another but during complete closure and the subsequent opening movement this hooking together is avoided.

The core 6 is non-rotatably connected to the sleeve 8. In order to provide this connection, the core bears in the embodiment of FIGS. 1 to 7 in the vicinity of its proximal end two pins 25 and 26 which penetrate the core 6 diametrically at a distance from one another and project in radial direction beyond the outer circumference of the core 6. The pin 25 arranged distally engages in longitudinal grooves 27 located opposite one another on the inner side of the sleeve 8 so that a non-rotatable connection results which does, however, make an axial displacement of the core 6 in relation to the sleeve 8 possible.

The pin 26 arranged proximally passes through a central opening 28 in the end wall 10 of the hood 9. This opening 28 has a circular cross section, the internal diameter of which corresponds to the external diameter of the core 6. At two diametrically opposite sides, this opening 28 has extensions 29 which are dimensioned such that the projecting ends of the pin 26 can pass through these extensions 29 when the core 6 is located in a specific angular position in relation to the tubular shaft 1; in all other angular positions, however, the pin 26 is supported on the edge of the opening 28 with the radially protruding parts. This support means that the core 6 can be displaced in distal direction in relation to the tubular shaft 1 only in the specific intermediate position and thus withdrawn out of the tubular shaft 1; in all other angular positions it is, however, locked with the tubular shaft 1 in axial direction as a result of this support.

The insertion depth of the core 6 into the tubular shaft 1 is, moreover, limited by the fact that the arm 7 of the core 6 abuts against the end face of the tubular shaft 1, the arm 7 thus forms a stop limiting the insertion depth.

The construction as described makes it possible to remove the core 6 with the arm 7 held thereon in a simple manner out of the instrument. For this purpose, it is sufficient to move the grip elements into an intermediate position, in which the proximal pin 26 is aligned with the extensions 29 of the opening 28. The pin 26 can then reach the interior of the tubular shaft 1 through the end wall 10 of the hood 9. This construction is thereby selected such that the longitudinal grooves 27 of the sleeve 8 are aligned with the extensions 29 in this specific angular position so that the pin 26 can also slide through these longitudinal grooves 27 of the sleeve 8 during any further distal displacement of the core 6.

During insertion of the core 6 into the tubular shaft, procedures are carried out in reverse order; it is then necessary to displace the grip elements 12 and 14 into the specific angular position, in which the longitudinal grooves 27 are aligned with the extensions 29 of the opening 28.

Figure 8:
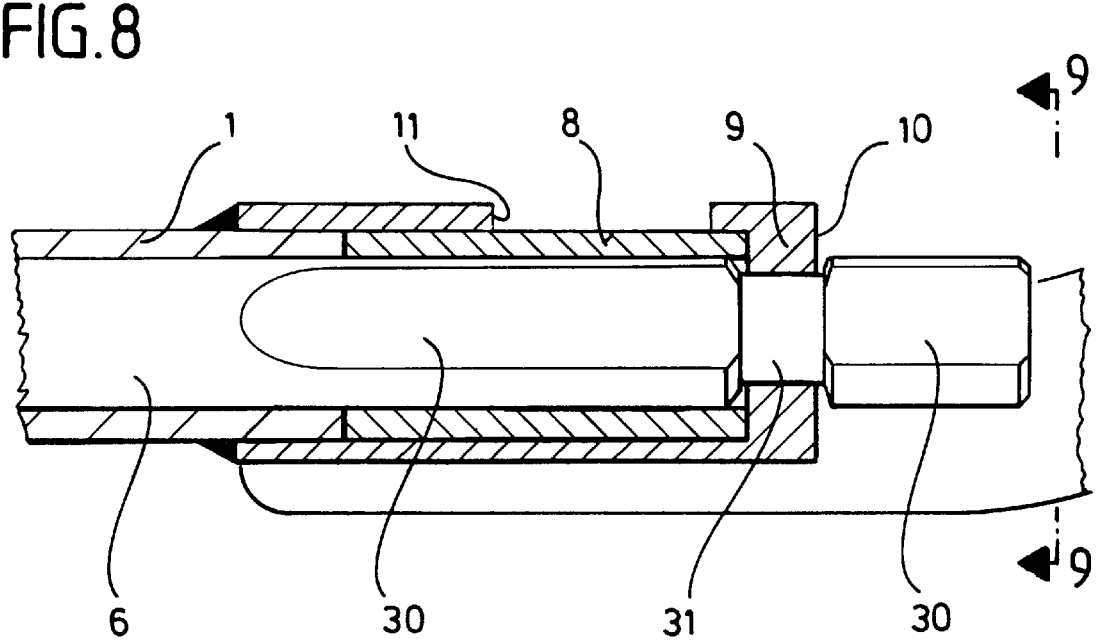
FIG. 8: a view similar to FIG. 4 of a modified example of a surgical instrument
Figure 9:
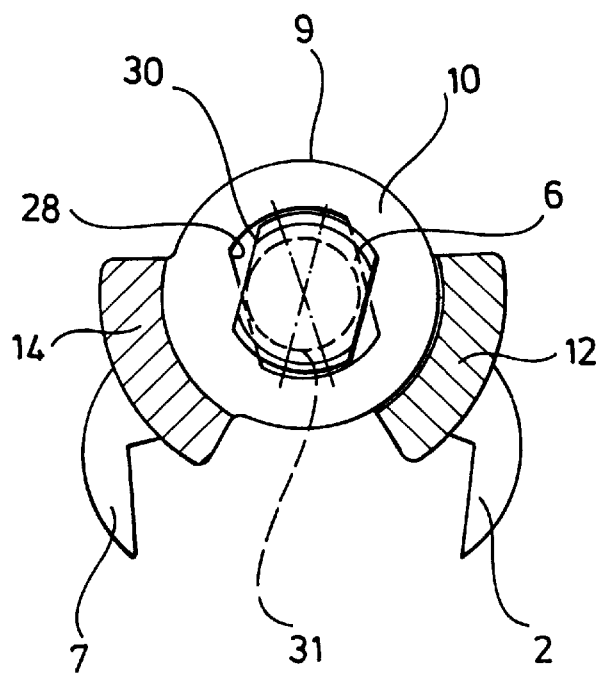
FIG. 9: a sectional view along line 9—9 in FIG. 8.

In the embodiment of FIGS. 1 to 7, the rotary entrainment coupling of the core 6 in relation to the sleeve 8 is achieved by means of a pin 25. In the embodiment of FIGS. 8 and 9, which is, for the rest, of a similar construction and in which parts corresponding to one another have the same reference numerals, the core 6 is provided in the region of the sleeve 8 with two flattened areas 30 located diametrically opposite one another, and the sleeve 8 has an internal cross section 31 complementary thereto so that a form-locking connection results between sleeve 8 and core 6.

In this embodiment, the opening 28 is, in addition, likewise of a complementary design to the flattened cross section of the core 6 so that this flattened cross section of the core 6 can pass through the opening 28 in a specific angular position. A section 31 of the core 6, which is located in the region of the end wall 10 when the core is inserted, has a circular cross section, the diameter of which corresponds to the diameter of the core in the flattened portion so that apart from in the specific angular position, in which the flattened cross section of the core 6 is aligned with the flattened cross section of the opening 28, an axial locking of the core in the tubular shaft results.

It would, of course, also be possible with this configuration to use other geometries of the cross section instead of the flattened areas; a precondition is merely that the cross section is non-circular on both sides of the section 31 so that,
on the one hand, the rotary entrainment with the sleeve 8 can take place and, on the other hand, a locking of the core against any distal displacement is possible when the core is not located in the specific angular position, in which it makes the distal displacement possible.

What is claimed is:

1. A surgical instrument comprising:

a tubular shaft, and two tools pivotable towards one another at a distal end of the shaft, said tools being pivotable relative to one another by means of a grip section at a proximal end of the tubular shaft via a transfer member arranged in the tubular shaft, wherein:

the pivot axis of the tools extends concentrically to a longitudinal axis of the tubular shaft, one of the tools is securely connected to the tubular shaft and the other of the tools is securely connected to the transfer member, the transfer member comprises a core mounted in the tubular shaft for rotation about the longitudinal axis, the grip section comprises two grip elements pivotable towards one another about a pivot axis, that extends concentrically to the longitudinal axis of the tubular shaft, one of the grip elements is securely connected to the tubular shaft and the other of the grip elements is securely connected to the core, and each of the grip elements has a gripping area extending parallel and laterally offset in relation to the longitudinal axis of the tubular shaft.

2. An instrument as defined in claim 1, wherein:

the grip elements are forced apart by a spring.

3. An instrument as defined in claim 2, wherein:

the spring comprises two clip springs abutting on one another, and said clip springs each form an extension of a respective one of said grip elements and are arranged to be laterally offset in relation to the pivot axis of the grip elements.

4. An instrument as defined in claim 1, wherein:

the grip elements are adapted to be fixed relative to one another in an intermediate position of their path of movement by means of a rotation blocking means.

5. An instrument as defined in claim 2, wherein:

the grip elements are adapted to be fixed relative to one another in an intermediate position of their path of movement by means of a rotation blocking means.

6. An instrument as defined in claim 3, wherein:

the grip elements are adapted to be fixed relative to one another in an intermediate position of their path of movement by means of a rotation blocking means.

7. An instrument as defined in claim 1, wherein:

a sleeve is mounted in the tubular shaft at its proximal end so as to be rotatable and axially nondisplaceable with respect to the tubular shaft, the tubular shaft has a window in an outer wall in a region of the sleeve, the sleeve is securely connected to one of the two grip elements through said window, and the sleeve is non-rotatably connected to the core.

8. An instrument as defined in claim 7, wherein:

the sleeve and the core are connected to one another as a result of a form-locking connection such that the core is nonrotatable but axially displaceable with respect to the sleeve.

9. An instrument as defined in claim 8, wherein:
the form-locking connection is formed by a tongue-and-groove connection.

10. An instrument as defined in claim 9, wherein:
the tongue is formed by at least one radially projecting pin.

11. An instrument as defined in claim 10, wherein:
the form-locking connection is formed by at least one flattened area of the circular cross section of the core and a complementary cross-sectional shape of the sleeve.

12. An instrument as defined in claim 8, wherein:
the core bears a stop limiting an insertion depth of the core into the tubular shaft in a direction of the proximal end.

13. An instrument as defined in claim 8, wherein:
the core bears a stop interacting with the tubular shaft, and
said stop securing secures the core completely inserted into the tubular shaft against any displacement in a direction of the distal end.

14. An instrument as defined in claim 13, wherein:
the stop is releasable.

15. An instrument as defined in claim 14, wherein:
the stop is slideable past the tubular shaft in an intermediate position of the rotary movement of the core in relation to the tubular shaft to make a displacement of the core in relation to the tubular shaft in distal direction possible only in this intermediate position.

16. An instrument as defined in claim 15, wherein:
the stop is a projection protruding radially from the core, and
said projection is aligned in the intermediate position with a radial extension of a central opening at the proximal end wall of the tubular shaft.

17. An instrument as defined in claim 16, wherein:
the projection comprises a radially projecting pin.

18. An instrument as defined in claim 15, wherein:
the core and the opening have a non-circular, complementary cross section congruent in the intermediate position.

19. An instrument as defined in claim 1, wherein: the two tools are designed as arms of a clip applicator.

* * * * *